United States Patent
Taubmann et al.

(10) Patent No.: US 11,529,110 B2
(45) Date of Patent: Dec. 20, 2022

(54) METHOD FOR OPERATING A MEDICAL IMAGING APPARATUS, MEDICAL IMAGING APPARATUS, COMPUTER PROGRAM AND ELECTRONICALLY READABLE STORAGE MEDIUM

(71) Applicant: Siemens Healthcare GmbH, Erlangen (DE)

(72) Inventors: Oliver Taubmann, Weilersbach (DE); Wladimir Lesyuk, Erlangen (DE); Michael Suehling, Erlangen (DE); Matthias May, Erlangen (DE); Michael Uder, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 106 days.

(21) Appl. No.: 17/019,511

(22) Filed: Sep. 14, 2020

(65) Prior Publication Data
US 2021/0093272 A1     Apr. 1, 2021

(30) Foreign Application Priority Data
Sep. 26, 2019 (EP) .................................... 19199875

(51) Int. Cl.
*A61B 6/03* (2006.01)
*A61B 6/00* (2006.01)
*G06N 3/08* (2006.01)

(52) U.S. Cl.
CPC ............. *A61B 6/469* (2013.01); *A61B 6/032* (2013.01); *A61B 6/468* (2013.01); *A61B 6/5205* (2013.01); *A61B 6/54* (2013.01); *G06N 3/08* (2013.01)

(58) Field of Classification Search
CPC .......... A61B 6/469; A61B 6/032; A61B 6/54; A61B 6/5205; A61B 6/468; A61B 5/055;
(Continued)

(56) References Cited

U.S. PATENT DOCUMENTS 8,781,062 B2 * 7/2014 Besson ................. G01N 23/04
378/19
2011/0229005 A1 9/2011 Den Harder et al.
(Continued)

FOREIGN PATENT DOCUMENTS

| EP | 0726542 A2 | 8/1996 |
|---|---|---|
| EP | 2194486 A1 | 6/2010 |

(Continued)

*Primary Examiner* — Don K Wong
(74) *Attorney, Agent, or Firm* — Harness, Dickey & Pierce, P.L.C.

(57) ABSTRACT

A method for operating a medical imaging apparatus includes acquiring a first image data set of a region of interest of the patient; automatically evaluating the first image data set using at least one evaluation algorithm yielding evaluation information, regarding at least one type of findings, describing a presence of at least one finding of the type requiring the acquisition of a second image data set and at least one imaging parameter for the second image data set; automatically notifying a user, upon the evaluation information indicating the presence of a required second image data set, of the required acquisition of the second image data set; and acquiring the second image data set acquiring the second image data set after confirmation of acquisition of the second image data set by the user, in a same examination process, using the at least one imaging parameter of the evaluation information.

18 Claims, 5 Drawing Sheets

(58) Field of Classification Search
CPC .... A61B 5/721; G06N 6/468; H04N 5/23229; H04N 5/2226; H04N 5/2723; H04N 5/23222; H04N 5/23212; G04N 5/2224; G06T 7/70; G06T 19/006
See application file for complete search history.

(56) References Cited

U.S. PATENT DOCUMENTS

2018/0060535 A1    3/2018   Reicher et al.
2019/0200963 A1    7/2019   Matsumoto

FOREIGN PATENT DOCUMENTS

EP           2374092 A1    10/2011
EP           3513738 A1     7/2019
WO    WO 2019/157214 A2    8/2019

\* cited by examiner

METHOD FOR OPERATING A MEDICAL IMAGING APPARATUS, MEDICAL IMAGING APPARATUS, COMPUTER PROGRAM AND ELECTRONICALLY READABLE STORAGE MEDIUM

PRIORITY STATEMENT

The present application hereby claims priority under 35 U.S.C. § 119 to European patent application number EP 19199875.6 filed Sep. 26, 2019, the entire contents of which are hereby incorporated herein by reference.

FIELD

Embodiments of the invention generally relate to a method for operating a medical imaging apparatus, comprising a control device, an input device and an output device, during an examination process of a patient; and a medical imaging apparatus, a computer program and an electronically readable storage medium.

BACKGROUND

In medical imaging, it is known to use a medical imaging apparatus employing at least one imaging modality to obtain image data sets of regions of interest of a patient. These image data sets are usually analysed by a radiologist, in particular some time after the image data set has been acquired. The analysis of the image data set may, for example, take place at a dedicated diagnostic work station. Later, findings or, if possible, even diagnosis, can be discussed with the patient.

However, many findings in image data sets acquired in examination processes of a patient cannot be fully interpreted on their own, in particular regarding chance findings. To complete the diagnostic process, additional image data sets are required, for example, using additional imaging techniques or focusing on the location of the finding. In the state of the art, the patient has to be invited for another examination process, wherein the medical imaging apparatus is manually configured to provide the additional image data required for the interpretation.

In an example, if the abdomen of an adult is imaged using computer tomography, in up to 5% of the image data sets a potential lesion of the adrenal gland is found. As such CT image data sets are usually analysed after the examination process of the patient has already been completed, a second image data set allowing for the diagnosis of the finding, for example regarding adenoma, metastasis and/or malign primary tumours, requires an additional examination process, such that a follow-up visit of the patient needs to be arranged. During this follow-up examination, for example, a so-called late washout scan requiring the administration of contrast agent may be performed.

SUMMARY

To sum up, the inventors have discovered that the diagnostic process is very slow and bothersome for the patient, in particular regarding additional medical appointments and the additional administration of contrast agent and the like.

At least one embodiment of the present invention improves the workflow in for examination of a patient, in particular regarding chance findings and/or other findings which are not sufficiently interpretable on their own.

Embodiments are directed to a method, a medical imaging apparatus, a computer program and an electronically readable storage medium. Advantageous embodiments are described in the claims.

In a computer-implemented method for operating a medical imaging apparatus, comprising a control device, an input device and an output device, during an examination process of a patient, according to an embodiment of the invention, the method comprises acquiring a first image data set of a region of interest of the patient, in the control device, automatically evaluating the first image data set using at least one evaluation algorithm yielding evaluation information regarding at least one type of findings, the evaluation information describing the presence of at least one finding of the at least one type in the first image data set, which requires the acquisition of a second image data set for further analysis, and at least one imaging parameter for the required second image data set, if the evaluation information indicates a required second image data set, automatically notifying a user of the required acquisition of the second image data set using the output device, and after receiving, from the input device, confirmation of the acquisition of the second image data set by the user, in the same examination process, acquiring the second image data set using the at least one imaging parameter of the evaluation information.

Generally, a method of an embodiment for providing the trained function comprises:

receiving input training data using a first training interface, receiving output training data using a second training interface, wherein the output training data is related to the input training data, training a function based on the input training data and the output training data using a training computation unit, and providing the trained function using a third training interface.

An embodiment of the invention further concerns a medical imaging apparatus, in particular computer tomography scanner, comprising a control device, an output device and an input device, wherein the control device is configured to perform the steps of a method according to an embodiment of the invention. All preferred embodiments and remarks regarding the method according to an embodiment of the invention correspondingly apply to the medical imaging apparatus.

In particular, the control device may comprise at least one processor and at least one storage device. In concrete embodiments, the control device may comprise an acquisition unit for controlling the acquisition of the first and second image data sets, an evaluation unit for determining the evaluation information and an input/output unit (I/O unit) for outputting the evaluation information and receiving confirmation from the user. Other functional units may be employed to realize further features of the invention.

A computer program according to at least one embodiment of the invention may be loaded into a storage device of a control device of a medical imaging apparatus and comprises instructions which, when the computer program is executed on the control device, cause the control device to carry out a method according to an embodiment of the invention. The computer program according to an embodiment of the invention may be stored on an electronically readable storage medium according to an embodiment of the invention, such that, when the electronically readable storage medium is used in a control device of a medical imaging apparatus, the control device carries out the steps of a method according to an embodiment of the invention. The electronically readably storage medium may be a non-transitory medium, for example a CD ROM.

According to at least one embodiment of the invention, a method, for operating a medical imaging apparatus including a control device, an input device and an output device, during an examination process of a patient, comprises:

acquiring a first image data set of a region of interest of the patient;

automatically evaluating the first image data set, in the control device, using at least one evaluation algorithm yielding evaluation information regarding at least one type of findings, the evaluation information describing a presence or absence of at least one finding of a type in the first image data set, requiring acquisition of a second image data set for further analysis, and at least one imaging parameter for the second image data set required;

automatically notifying a user, upon the evaluation information indicating the presence of a required second image data set, of the required acquisition of the second image data set using the output device; and acquiring the second image data set acquiring the second image data set after confirmation of acquisition of the second image data set by the user, in a same examination process, using the at least one imaging parameter of the evaluation information.

According to at least one embodiment of the invention, a medical imaging apparatus, comprises:

a control device;
an input device; and
an output device, the control device being configured to perform at least:

acquiring a first image data set of a region of interest of the patient;

automatically evaluating the first image data set, in the control device, using at least one evaluation algorithm yielding evaluation information regarding at least one type of findings, the evaluation information describing a presence or absence of at least one finding of a type in the first image data set, requiring acquisition of a second image data set for further analysis, and at least one imaging parameter for the second image data set required;

automatically notifying a user, upon the evaluation information indicating the presence of a required second image data set, of the required acquisition of the second image data set using the output device; and acquiring the second image data set acquiring the second image data set after confirmation of acquisition of the second image data set by the user, in a same examination process, using the at least one imaging parameter of the evaluation information.

At least one embodiment is directed to a non-transitory computer program, comprising instructions which, when the computer program is executed on a control device of a medical imaging apparatus, cause the control device to carry out the method of an embodiment.

At least one embodiment is directed to a non-transitory electronically readable storage medium, storing computer program comprising instructions which, when the computer program is executed on a control device of a medical imaging apparatus, cause the control device to carry out the method of an embodiment.

BRIEF DESCRIPTION OF THE DRAWINGS

Other objects and features of the present invention will become apparent from the following detailed description considered in conjunction with the accompanying drawings. The drawings, however, are only principle sketches designed solely for the purpose of illustration and do not limit the invention. The drawings show.

DETAILED DESCRIPTION OF THE EXAMPLE EMBODIMENTS

Figure 1:
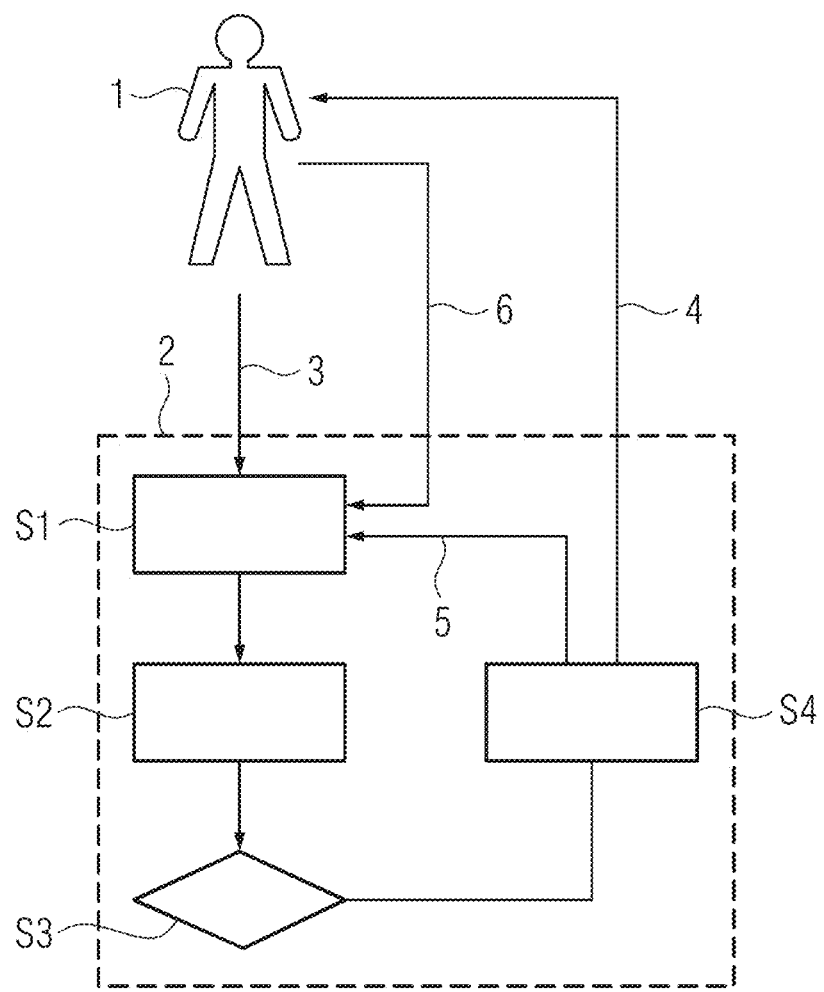
FIG. 1 a flowchart showing an embodiment of a method according to the invention, FIG. 2 an embodiment of an artificial neural network, FIG. 3 an embodiment of a convolutional neural network, FIG. 4 a concrete topology of a deep neural network for segmentation of findings in the adrenal gland, FIG. 5 a schematic drawing of a medical imaging apparatus according to an embodiment of the invention, and FIG. 6 the functional structure of a control device of the medical imaging apparatus according to FIG. 5.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In a computer-implemented method for operating a medical imaging apparatus, comprising a control device, an input device and an output device, during an examination process of a patient, according to an embodiment of the invention, the method comprises acquiring a first image data set of a region of interest of the patient, in the control device, automatically evaluating the first image data set using at least one evaluation algorithm yielding evaluation information regarding at least one type of findings, the evaluation information describing the presence of at least one finding of the at least one type in the first image data set, which requires the acquisition of a second image data set for further analysis, and at least one imaging parameter for the required second image data set, if the evaluation information indicates a required second image data set, automatically notifying a user of the required acquisition of the second image data set using the output device, and after receiving, from the input device, confirmation of the acquisition of the second image data set by the user, in the same examination process, acquiring the second image data set using the at least one imaging parameter of the evaluation information.

In the method according to an embodiment of the invention, the first image data set of the patient is acquired as known, for example controlled by an acquisition unit of the control device. Immediately after the acquisition, in particular while the patient is still positioned in the medical imaging apparatus, the first image data set is automatically analysed in the control device using at least one evaluation algorithm, which, in essence, searches for the presence of findings of at least one type in the first image data set. The presence of these findings is an intermediate result, which, in particular, does not suffice for a diagnosis, such that additional information in form of a second image data set is required. The further information provided by the second image data set may, for example, allow for distinguishing image artefacts and/or non-malign anatomical structures from diagnostically relevant lesions. In other words, the at least one evaluation algorithm is looking for findings of a type which inspires further imaging of the finding. The findings are features, for example physical characteristics of anatomical structures and/or results of the imaging process, which require further information, in this case the second image data set, for their interpretation. For example, the finding may be a potential lesion and/or a potential image artefact.

In summary, an embodiment of the present invention proposes an automatic detection of findings which require further diagnostic imaging. Such findings may also be called "actionable findings". The evaluation is performed in the background after the first image data set was acquired, in particular immediately following the scan. If the result is positive, that is, a finding is present, the results are immediately output, for example at a user interface of the medical imaging apparatus. This allows for performing the acquisition of the second image data set, which may be called a work-up step, without delay. To support this workflow, at least one suitable imaging parameter, in most cases more than one imaging parameter, is also automatically determined, such that the medical imaging apparatus can be easily configured for the acquisition of the second image data set. In advantageous embodiments, the at least one imaging parameter may define a complete acquisition protocol for the medical imaging apparatus, allowing for completely automatic acquisition of the second image data set. Such acquisition protocols are already known in the state of the art and may also be employed here, in particular adapted regarding the type and/or properties of the finding and/or adapted to the current patient.

In some cases, a further acquisition may already be planned during the current examination of the patient, and it may be possible to modify this further examination to yield the second image data set. In other words, in the case that a further acquisition was already planned during this examination, the further examination may be modified depending on at least one of the at least one imaging parameter to yield the second image data set. This modification may, in some cases, also relate to the reconstruction only. In such an embodiment, no additional scan needs to be added, but an already planned further acquisition is modified to be suitable to work-up the actionable finding. However, the user is still advantageously notified regarding this change and the necessity of the second image data set. Often, however, the acquisition of the second image data set may, as described, be an additional, new scan.

It is generally noted that multiple evaluation algorithms may be used for different types of findings, while it is also possible to use one evaluation algorithm to detect the presence of multiple types of findings. For example, if the region of interest comprises several anatomical structures, findings in different anatomical structures may be differentiated and/or multiple types of findings for a certain anatomical structure may be distinguished. All those different types of findings may require different additional information and thus different imaging parameters, in particular acquisition protocols, for the second image data set. Hence, imaging parameters may be allocated to certain types of findings.

Imaging parameters may, for example, describe which imaging technique to use, the field of view, contrast settings and the like. Imaging parameters may further comprise reconstruction parameters, and/or information regarding contrast agents. When the evaluation information is output to the user, if further preconditions, for example regarding the contrast agent, are required, the user is also accordingly notified.

In summary, according to an embodiment of the present invention, a work-up scan acquiring the second image data set can immediately be performed and its configuration is simple, fast and standardized. The risk to overlook "actionable findings" is reduced. The current invention also contributes to the establishment of an "intelligent scanner".

Additionally, time and cost are saved, since an additional summoning of the patient is unnecessary. If contrast agent has been administered to the patient regarding the acquisition of the first image data set, in some circumstances, no further contrast agent needs to be administered. For example, a so-called late washout scan may be performed using the contrast agent already administered. This leads to a further reduction of cost and time and contributes to the well-being of the patient.

These advantages are achieved by automatically detecting "actionable findings" in the medical imaging apparatus, by the immediate notification and guidance for the user and the automatic configuration of the work-up scan, that is, the acquisition of the second image data set.

While, in preferred embodiments, the medical imaging apparatus may be a computer tomography scanner, an embodiment of the invention may also be applied to other modalities, for example a magnetic resonance scanner, a PET imaging device, and the like. In some embodiments, the medical imaging apparatus may also be a dual-modality scanner.

The acquisition of the second image data set is proposed to the user during the examination process via the output device. The medical imaging apparatus further comprises an input device, wherein the output device and the input device may form a user interface and/or be part of a workstation of the medical imaging apparatus. The user may confirm the acquisition of the second image data set using the input device, for example by pressing a confirmation button. In the preferable case in which the imaging parameters of the evaluation information enable the fully automatic acquisition of the second image data set, the acquisition may immediately or, respecting a certain timing, in particular relating to a contrast agent, ensue.

It is, however, also possible that the at least one imaging parameter and/or additional imaging parameters are modified and/or defined depending on user input. That is, the user retains full control regarding the acquisition processes and may modify or add imaging parameters.

In an especially preferred embodiment of the present invention, at least one of the at least one evaluation algorithm comprises a trained function trained by a machine learning algorithm, wherein the trained function in particular comprises a deep neural network.

In general, a trained function mimics cognitive functions that humans associate with other human minds. In particular, by training based on training data, the trained function is able to adapt to new circumstances and to detect and extrapolate patterns. The trained function may, in particular, be an artificial intelligence algorithm.

In general, parameters of a trained function can be adapted by way of training. In particular, supervised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, the trained function can comprise a neural network, a support vector machine, a decision tree and/or a Bayesian network, and/or the trained function can be based on K-means clustering, Q-learning, genetic algorithms and/or association rules. In particular, a neural network can be a deep neural network, a convolutional neural network or a convolutional deep neural network. Furthermore, a neural network can be an adversarial network, a deep adversarial network and/or a generative adversarial network.

Regarding the trained function of the at least one evaluation algorithm, the trained function may be trained using annotated training data sets of the region of interest or sub-regions thereof. In many cases, the input data of the trained function may comprise image data of the first image data set. The output data may, for example, comprise modified image data, image-like data and/or other values, for example a general probability for the presence of a finding. Regarding the training of the function, input training data may comprise image data of the modality of the medical imaging apparatus, to which, for example by annotation, output training data has been associated. Input training data and output training data may form a training data set.

In preferred embodiments, the input data for the trained function may comprise image data, in particular image data of the first image data set, and/or the output data may comprise at least one probability for the presence of a finding of the at least one type. For example, when the input data comprises slice images and/or sectional images, the output data may comprise corresponding probability images, in which to each data point, in particular pixel or voxel, a probability that a finding of the at least one type is present is assigned.

Generally, a method of an embodiment for providing the trained function comprises:

receiving input training data using a first training interface, receiving output training data using a second training interface, wherein the output training data is related to the input training data, training a function based on the input training data and the output training data using a training computation unit, and providing the trained function using a third training interface.

As already explained, the input training data may preferably comprise image data of the same modality as the medical imaging apparatus and the output training data may be annotation data associated with the image data.

Preferably, for at least one of the at least one of the at least one evaluation algorithm analysing at least one anatomical structure, image data showing the anatomical structure are extracted from the first image data set. In the following, only the extracted image data are analysed by this evaluation algorithm. For example, a landmark-based extraction may be performed. It is noted that, already in this context, artificial intelligence may be employed, for example by using a trained extraction function to extract the image data of the anatomical structure. For example, if the first image data set comprises an axial stack of two-dimensional sectional or slice images, a learning-based landmark detection may be employed to extract the relevant axial image region showing the anatomical structure. It is noted that not all of the anatomical structure has to be included in the extracted image data.

In an especially preferred embodiment, at least a part of at least one of the at least one evaluation algorithm, in particular the trained function, determines, for each data point in the analysed image data, a probability that the data point belongs to a finding of the at least one type. For example, the trained function may receive image data of the first image data set as input data, that is, image data values for certain image data points, in particular extracted pixels or voxels or even all pixels or voxels. In particular, the input data may, as discussed above, be only a part of the first image data set, for example at least one sectional or slice image. The output data of the trained function (or, generally, the part) is a probability image, which contains at least one probability value for each data point. If multiple types of findings are detected by the respective evaluation algorithm, probabilities for each type of finding may be determined separately.

In concrete embodiments, if the input data comprises sectional or slice images, each sectional or slice image may be separately input to the trained function, yielding a corresponding probability image. Regarding the use of artificial intelligence, a suitable topology for image segmentation problems may be used. To detect the presence of a finding, preferably, it can be checked whether the maximum of the probabilities exceeds a first threshold value, such that the presence of a finding is determined when the first threshold value is exceeded by the maximum of the probabilities. In an advantageous embodiment, outlier detection may be applied to the probabilities, in particular a probability image, to exclude segmentation errors.

In particular in the case that a probability for each data point of the input image data is determined separately, such that a probability image results as output data, if the presence of a finding is determined, the position of the data point of the maximum probability can be determined as the location of the finding and/or an area surrounding the data point of the maximum probability, where the probability exceeds a second threshold, can be determined as an extension of the finding.

Generally spoken, in advantageous embodiments, at least one of the at least one evaluation algorithm additionally determines finding information describing a finding whose presence has been determined, in particular a location and/or extension and/or a characterization of the finding, wherein at least one of the at least one imaging parameter is chosen and/or adapted depending on the finding information. The determination of more information regarding the finding, apart from its presence, allows to, so to say, "tailor" the imaging parameters for the acquisition of the second image data set to the concrete finding, such that the second image data set forms an outstanding basis to later determine the nature of the finding. For example, when calculating probability images, the position where the maximum probability is found may be used as a location of the lesion, while the set of data points, in particular pixels and/or voxels, surrounding this location, for which the probability exceeds a second threshold, may quantify the extension, that is, the dimensions, of the finding as well as its posture. Such finding information may, for example, be used to determine imaging parameters describing a suitable field of view.

Regarding other finding information, which, for example, characterizes the finding, for example, a malignancy probability may be determined. In this context, it is, again, possible to employ artificial intelligence, in particular a trained characterizing function. In this case, the topology of the trained characterizing function may be chosen as one suitable for image classification problems. Training data sets may, in this case, for example comprise annotated image data of benign and malign lesions and/or image artifacts.

In an embodiment of the present invention, the finding information may not only be used to adapt or define certain imaging parameters, but it is also conceivable to output at least a part of the finding information to the user during notification. In this manner, the user is provided with all necessary information to decide on confirmation or non-confirmation regarding the acquisition of a second image data set.

In preferred embodiments, the image data set may be acquired using computer tomography, in particular multi-energy computer tomography. In this case, the medical imaging apparatus is a computer tomography scanner. Regarding multi-energy data, it can be advantageously used to characterize certain findings. However, the invention may also be applied to other modalities, in particular magnetic resonance imaging.

An embodiment of the invention further concerns a medical imaging apparatus, in particular computer tomography scanner, comprising a control device, an output device and an input device, wherein the control device is configured to perform the steps of a method according to an embodiment of the invention. All preferred embodiments and remarks regarding the method according to an embodiment of the invention correspondingly apply to the medical imaging apparatus.

In particular, the control device may comprise at least one processor and at least one storage device. In concrete embodiments, the control device may comprise an acquisition unit for controlling the acquisition of the first and second image data sets, an evaluation unit for determining the evaluation information and an input/output unit (I/O unit) for outputting the evaluation information and receiving confirmation from the user. Other functional units may be employed to realize further features of the invention.

A computer program according to at least one embodiment of the invention may be loaded into a storage device of a control device of a medical imaging apparatus and comprises instructions which, when the computer program is executed on the control device, cause the control device to carry out a method according to an embodiment of the invention. The computer program according to an embodiment of the invention may be stored on an electronically readable storage medium according to an embodiment of the invention, such that, when the electronically readable storage medium is used in a control device of a medical imaging apparatus, the control device carries out the steps of a method according to the invention. The electronically readably storage medium may be a non-transitory medium, for example a CD ROM.

FIG. 1 shows a schematic flow chart of a method according to an embodiment of the invention. For better explanation, the domains of the user 1 and a medical imaging apparatus 2 (scanner) are indicated. The medical imaging apparatus 2 may, for example, be the computer tomography scanner or a magnetic resonance scanner.

The steps illustrated in FIG. 1 all take place during a single examination process of a patient. That is, a patient is positioned in an imaging volume of the medical imaging apparatus 2, for example in the gantry of a computer tomography scanner or the bore of a magnetic resonance scanner. After the patient is positioned, the user 1 sets up the acquisition of a first image data set, according to arrow 3.

In a step S1, an acquisition unit of the control device of the medical imaging apparatus 2 uses the imaging parameters provided by the user 1 to acquire the first image data set of the patient. The first image data set of the patient may, for example, be a reconstructed computer tomography data set showing a region of interest of the patient, for example the abdomen, the head or the like. Once the acquisition of the first image data set is completed, including reconstruction steps, step S2 is automatically triggered, in particular while the patient still remains positioned in the medical imaging apparatus 2.

In step S2, the control device, for example an evaluation unit of the control device, evaluates the first image data set automatically in real-time to detect so-called "actionable findings". At least one evaluation algorithm is employed to detect the presence of findings which, for a complete analysis, require the acquisition of further image data of the patient, in particular a certain second image data set. In concrete embodiments, multiple types of findings may be detected, wherein each type of finding may be associated with certain imaging parameters for the corresponding second image data set. As a result of step S2, the evaluation unit outputs an evaluation information, which indicates whether a finding is present and, if a finding is present, which imaging parameters, preferably forming a complete acquisition protocol, are expedient to acquire the corresponding second image data set. The evaluation information may further comprise finding information describing the finding, wherein such finding information is preferably also used to adapt or chose certain imaging parameters, such that, for example, a suitable contrast is given and/or the field of view for the second image data set is set correctly.

If, in step S3, it is determined that a finding requiring the acquisition of a second image data set is present, the user is notified in step S4 using the output device of a user interface, in this case a workstation, of the medical imaging apparatus 2. This notification is also indicated by arrow 4 and takes place immediately after the end of the evaluation in step S2, such that the patient is still positioned in the medical imaging apparatus 2. The notification also displays the evaluation information, in particular not only the fact that a second scan seems expedient because of a finding, but also the proposed imaging parameters as well as finding information, if it was determined as part of the evaluation information. Also, in step S4, in parallel to the notification, the medical imaging apparatus 2 is pre-configured corresponding to the imaging parameters of the evaluation information, as indicated by arrow 5.

On the output device, for example a monitor of a scanner work station, the user 1 is also asked to confirm that the second image data set of the patient is to be acquired. The user may now confirm the acquisition of the second image data set and/or may adjust imaging parameters for the acquisition of the second image data set, as indicated by arrow 6. To this end, the user 1 uses an input device of the user interface of the medical imaging apparatus 2.

After confirmation, the acquisition unit of the control device acquires the second image data set in step S1.

In the embodiment of FIG. 1, at least one of the at least one evaluation algorithm uses artificial intelligence, in particular a trained function, which may be implemented as a neural network. Prior to explaining a concrete example, a general description of neural networks shall be given with respect to FIGS. 2 and 3.

Figure 2:
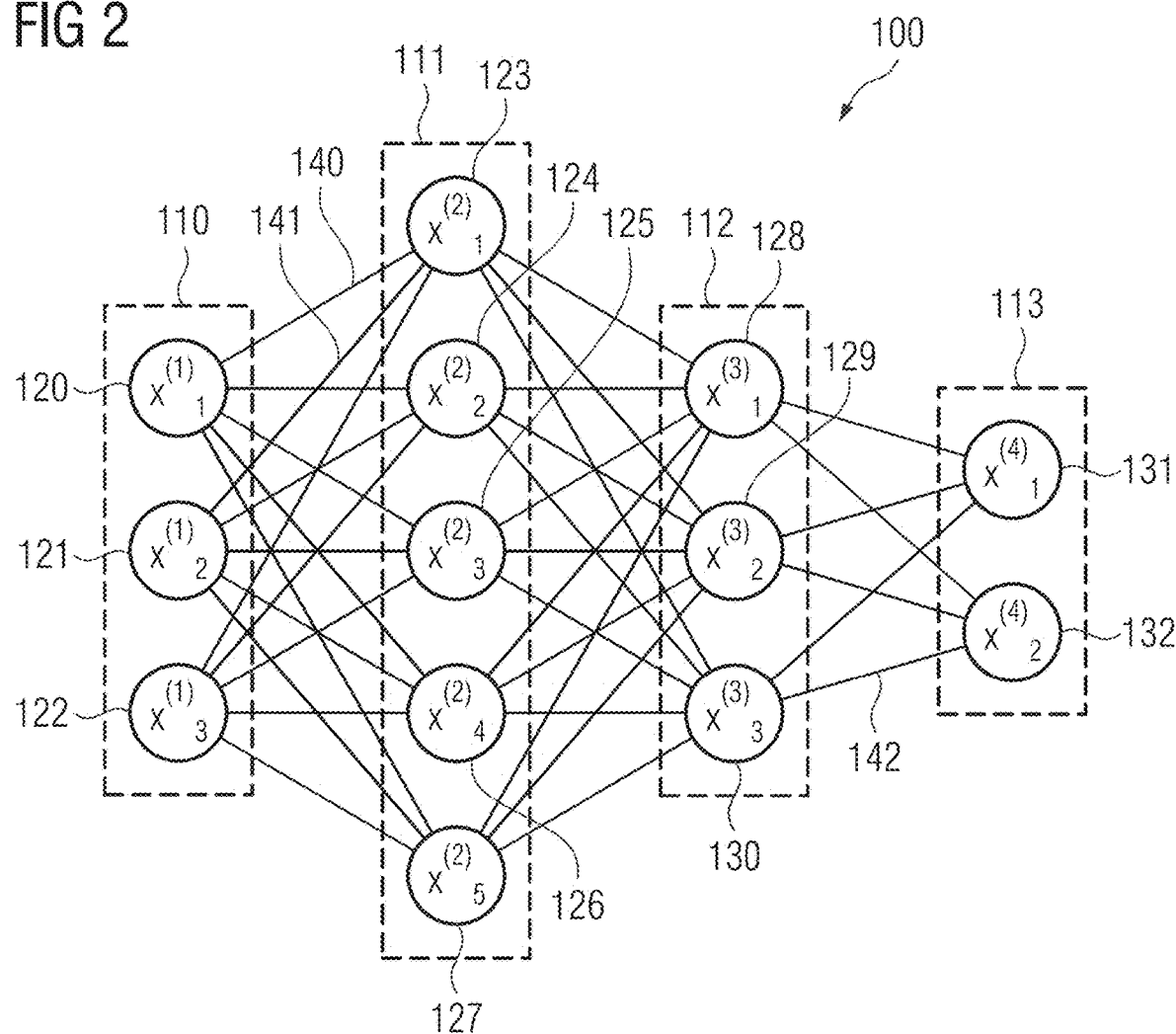

FIG. 2 displays an embodiment of an artificial neural network 100. Alternative terms for "artificial neural network" are "neural network", "artificial neural net" or "neural net".

The artificial neural network 100 comprises nodes 120, ..., 132 and edges 140, ..., 142, wherein each edge 140, ..., 142 is a directed connection from a first node 120, ..., 132 to a second node 120, ..., 132. In general, the first node 120, ..., 132 and the second node 120, ..., 132 are different nodes 120, ..., 132, it is also possible that the first node 120, ..., 132 and the second node 120, ..., 132 are identical. For example, in FIG. 1 the edge 140 is a directed connection from the node 120 to the node 123, and the edge 142 is a directed connection from the node 130 to the node 132. An edge 140, ..., 142 from a first node 120, ..., 132 to a second node 120, ..., 132 is also denoted as "ingoing edge" for the second node 120, ..., 132 and as "outgoing edge" for the first node 120, ..., 132.

In this embodiment, the nodes 120, ..., 132 of the artificial neural network 100 can be arranged in layers 110, ..., 113, wherein the layers can comprise an intrinsic order introduced by the edges 140, ..., 142 between the nodes 120, ..., 132. In particular, edges 140, ..., 142 can exist only between neighboring layers of nodes. In the displayed embodiment, there is an input layer 110 comprising only nodes 120, ..., 122 without an incoming edge, an output layer 113 comprising only nodes 131, 132 without outgoing edges, and hidden layers 111, 112 in-between the input layer 110 and the output layer 113. In general, the number of hidden layers 111, 112 can be chosen arbitrarily. The number of nodes 120, ..., 122 within the input layer 110 usually relates to the number of input values of the neural network, and the number of nodes 131, 132 within the output layer 113 usually relates to the number of output values of the neural network.

In particular, a (real) number can be assigned as a value to every node 120, ..., 132 of the neural network 100. Here, x(n)i denotes the value of the i-th node 120, ..., 132 of the n-th layer 110, ..., 113. The values of the nodes 120, ..., 122 of the input layer 110 are equivalent to the input values of the neural network 100, the values of the nodes 131, 132 of the output layer 113 are equivalent to the output value of the neural network 100. Furthermore, each edge 140, ..., 142 can comprise a weight being a real number, in particular, the weight is a real number within the interval [−1, 1] or within the interval [0, 1]. Here, $w^{(m,n)}_{i,j}$ denotes the weight of the edge between the i-th node 120, ..., 132 of the m-th layer 110, ..., 113 and the j-th node 120, ..., 132 of the n-th layer 110, ..., 113. Furthermore, the abbreviation $w^{(n)}_{i,j}$ is defined for the weight $w^{(n,n+1)}_{i,j}$.

In particular, to calculate the output values of the neural network 100, the input values are propagated through the neural network. In particular, the values of the nodes 120, ..., 132 of the (n+1)-th layer 110, ..., 113 can be calculated based on the values of the nodes 120, ..., 132 of the n-th layer 110, ..., 113 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 110 are given by the input of the neural network 100, wherein values of the first hidden layer 111 can be calculated based on the values of the input layer 110 of the neural network, wherein values of the second hidden layer 112 can be calculated based in the values of the first hidden layer 111, etc.

In order to set the values $w^{(m,n)}_{i,j}$ for the edges, the neural network 100 has to be trained using training data. In particular, training data comprises training input data and training output data (denoted as $t_i$). For a training step, the neural network 100 is applied to the training input data to generate calculated output data. In particular, the training data and the calculated output data comprise a number of values, the number being equal with the number of nodes of the output layer.

In particular, a comparison between the calculated output data and the training data is used to recursively adapt the weights within the neural network 100 (backpropagation algorithm). In particular, the weights are changed according to $$w'^{(n)}_{i,j} = w_{i,j}^{(n)} - \gamma \cdot \delta_j^{(n)} \cdot x_i^{(n)}$$

wherein $\gamma$ is a learning rate, and the numbers $\delta^{(n)}_j$ can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)}=(x_k^{(n+1)}-t_j^{(n+1)})\cdot f'(\Sigma_i x_i^{(n)}\cdot w_{i,j}^{(n)})$$

if the (n+1)-th layer is the output layer 113, wherein f' is the first derivative of the activation function, and $y^{(n+1)}_j$ is the comparison training value for the j-th node of the output layer 113.

Figure 3:
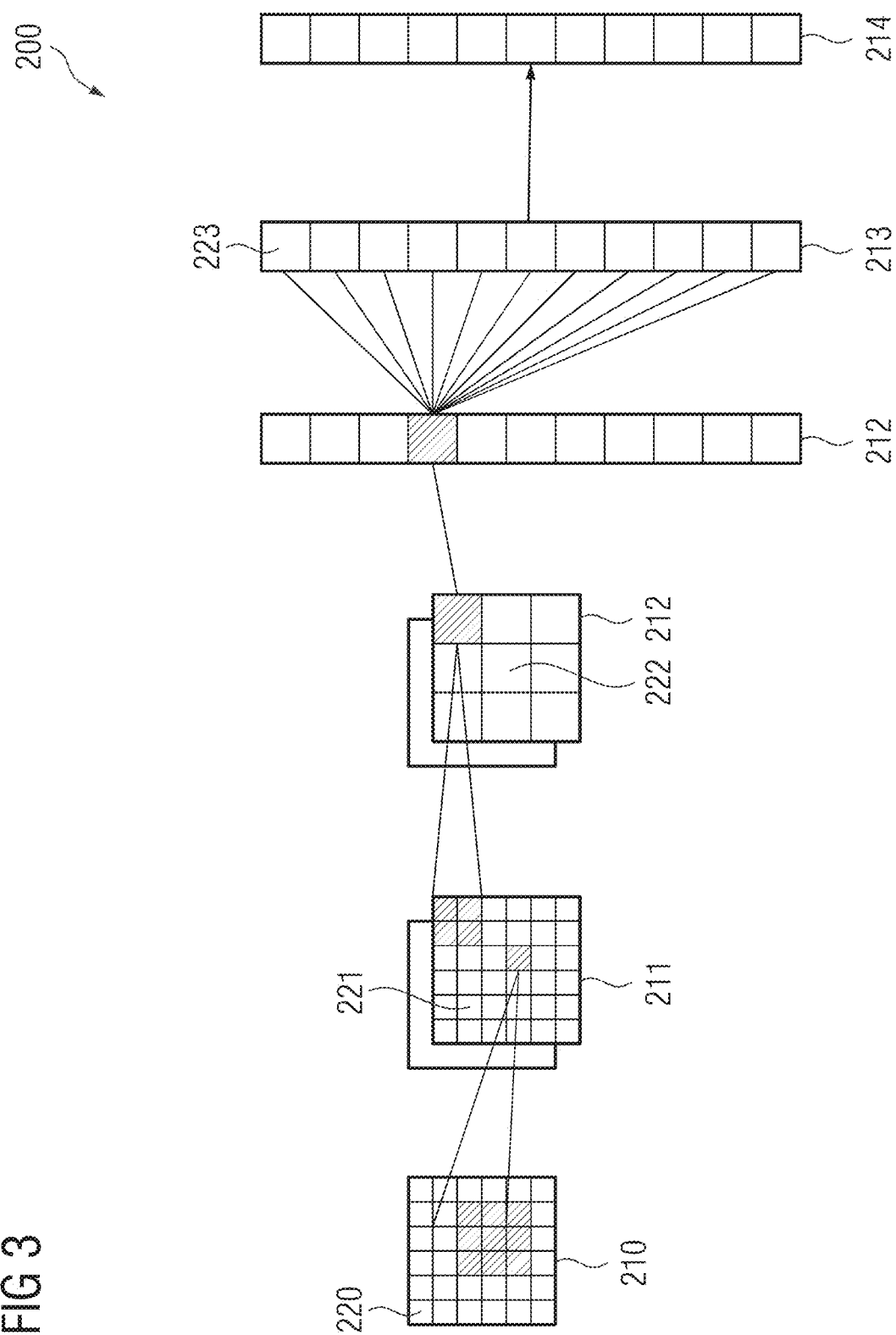

In FIG. 3, an embodiment of a convolutional neural network 200 is shown. It is noted that the use of the term "layer" differs between classical neural networks and convolutional neural networks. For a classical neural network, the term "layer" refers only to the set of nodes forming a layer (a certain "generation" of nodes). For a convolutional neural network, the term "layer" is often used as an object that actively transforms data, in other words as a set of nodes of the same "generation" and either the set of incoming or the set of outgoing nodes.

FIG. 3 displays an embodiment of a convolutional neural network 200. In the displayed embodiment, the convolutional neural network 200 comprises an input layer 210, a convolutional layer 211, a pooling layer 212, a fully connected layer 213 and an output layer 214. Alternatively, the convolutional neural network 200 can comprise several convolutional layers 211, several pooling layers 212 and several fully connected layers 213, as well as other types of layers. The order of the layers can be chosen arbitrarily, usually fully connected layers 213 are used as the last layers before the output layer 214.

In particular, within a convolutional neural network 200 the nodes 220, . . . , 224 of one layer 210, . . . , 214 can be considered to be arranged as a d-dimensional matrix or as a d-dimensional image. In particular, in the two-dimensional case the value of the node 220, . . . , 224 indexed with i and j in the n-th layer 210, . . . , 214 can be denoted as $x^{(n)}[i,j]$. However, the arrangement of the nodes 220, . . . , 224 of one layer 210, . . . , 214 does not have an effect on the calculations executed within the convolutional neural network 200 as such, since these are given solely by the structure and the weights of the edges.

In particular, a convolutional layer 211 is characterized by the structure and the weights of the incoming edges forming a convolution operation based on a certain number of kernels. In particular, the structure and the weights of the incoming edges are chosen such that the values $x^{(n)}_k$ of the nodes 221 of the convolutional layer 211 are calculated as a convolution $x^{(n)}_k=K_k*x^{(n-1)}$ based on the values $x^{(n-1)}$ of the nodes 220 of the preceding layer 210, where the convolution is defined in the two-dimensional case as $$x_k^{(n)}[i,j]=(K_k*x^{(n-1)})[i,j]=\Sigma_{i'}\Sigma_{j'}K_k[i',j']\cdot x^{(n-1)}[i-i',j-j'].$$

Here the k-th kernel $K_k$ is a d-dimensional matrix (in this embodiment a two-dimensional matrix), which is usually small compared to the number of nodes 220, . . . , 224 (e.g. a 3×3 matrix, or a 5×5 matrix). In particular, this implies that the weights of the incoming edges are not independent, but chosen such that they produce the convolution equation. In particular, for a kernel being a 3×3 matrix, there are only 9 independent weights (each entry of the kernel matrix corresponding to one independent weight), irrespectively of the number of nodes 220, . . . , 224 in the respective layer 210, . . . , 214. In particular, for a convolutional layer 211 the number of nodes 221 in the convolutional layer is equivalent to the number of nodes 220 in the preceding layer 210 multiplied with the number of kernels.

If the nodes 220 of the preceding layer 210 are arranged as a d-dimensional matrix, using a plurality of kernels can be interpreted as adding a further dimension (denoted as "depth" dimension), so that the nodes 221 of the convolutional layer 221 are arranged as a (d+1)-dimensional matrix. If the nodes 220 of the preceding layer 210 are already arranged as a (d+1)-dimensional matrix comprising a depth dimension, using a plurality of kernels can be interpreted as expanding along the depth dimension, so that the nodes 221 of the convolutional layer 221 are arranged also as a (d+1)-dimensional matrix, wherein the size of the (d+1)-dimensional matrix with respect to the depth dimension is by a factor of the number of kernels larger than in the preceding layer 210.

The advantage of using convolutional layers 211 is that spatially local correlation of the input data can exploited by enforcing a local connectivity pattern between nodes of adjacent layers, in particular by each node being connected to only a small region of the nodes of the preceding layer.

In the displayed embodiment, the input layer 210 comprises 36 nodes 220, arranged as a two-dimensional 6×6 matrix. The convolutional layer 211 comprises 72 nodes 221, arranged as two two-dimensional 6×6 matrices, each of the two matrices being the result of a convolution of the values of the input layer with a kernel. Equivalently, the nodes 221 of the convolutional layer 211 can be interpreted as arranges as a three-dimensional 6×6×2 matrix, wherein the last dimension is the depth dimension.

A pooling layer 212 can be characterized by the structure and the weights of the incoming edges and the activation function of its nodes 222 forming a pooling operation based on a non-linear pooling function f. For example, in the two dimensional case the values $x^{(n)}$ of the nodes 222 of the pooling layer 212 can be calculated based on the values $x^{(n-1)}$ of the nodes 221 of the preceding layer 211 as $$x^{(n)}[i,j]=f(x^{(n-1)}[id_1,jd_2],\ \ldots\ x^{(n-1)}[id_1+d_1-1,jd_2+d_2-1])$$

In other words, by using a pooling layer 212 the number of nodes 221, 222 can be reduced, by replacing a number $d_1\cdot d_2$ of neighboring nodes 221 in the preceding layer 211 with a single node 222 being calculated as a function of the values of the number of neighboring nodes in the pooling layer. In particular, the pooling function f can be the max-function, the average or the L2-Norm. In particular, for a pooling layer 212 the weights of the incoming edges are fixed and are not modified by training.

The advantage of using a pooling layer 212 is that the number of nodes 221, 222 and the number of parameters is reduced. This leads to the amount of computation in the network being reduced and to a control of overfitting.

In the displayed embodiment, the pooling layer 212 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 213 can be characterized by the fact that a majority, in particular, all edges between nodes 222 of the previous layer 212 and the nodes 223 of the fully-connected layer 213 are present, and wherein the weight of each of the edges can be adjusted individually.

In this embodiment, the nodes 222 of the preceding layer 212 of the fully-connected layer 213 are displayed both as two-dimensional matrices, and additionally as non-related nodes (indicated as a line of nodes, wherein the number of nodes was reduced for a better presentability). In this embodiment, the number of nodes 223 in the fully connected layer 213 is equal to the number of nodes 222 in the preceding layer 212. Alternatively, the number of nodes 222, 223 can differ.

Furthermore, in this embodiment the values of the nodes 224 of the output layer 214 are determined by applying the Softmax function onto the values of the nodes 223 of the preceding layer 213. By applying the Softmax function, the sum of the values of all nodes 224 of the output layer is 1, and all values of all nodes 224 of the output layer are real numbers between 0 and 1. In particular, if using the convolutional neural network 200 for categorizing input data, the values of the output layer can be interpreted as the probability of the input data falling into one of the different categories.

A convolutional neural network 200 can also comprise a ReLU (acronym for "rectified linear units") layer. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer. Examples for rectifying functions are $f(x)=\max(0,x)$, the tangent hyperbolics function or the sigmoid function.

In particular, convolutional neural networks 200 can be trained based on the backpropagation algorithm. For preventing overfitting, methods of regularization can be used, e.g. dropout of nodes 220, . . . , 224, stochastic pooling, use of artificial data, weight decay based on the L1 or the L2 norm, or max norm constraints.

While embodiments of the current invention may be applied to different types of findings and different regions of interest, in the following, a learning-based evaluation algorithm, in particular comprising one deep neural network as a trained function, which detects findings in the adrenal glands in a first image data set of the abdomen of a patient, shall be presented. The evaluation algorithm is configured to detect, quantify and potentially characterize a finding, for example a potential lesion, a potential artefact and/or potential properties of an adrenal gland, for example potentially hypertrophic adrenal glands. The evaluation algorithm is applied by the control device automatically after each thorax and/or abdomen scan of the patient. If the result is positive, that is, the evaluation information indicates the presence of a finding, the user is notified on the user interface and it is proposed to perform a late wash out scan for acquisition of the second image data set, which is also (in step S4 of FIG. 1) already pre-configured.

In a first step of the evaluation algorithm for the adrenal glands, the relevant image data is extracted from the first image data set, i.e. image data showing the adrenal gland as anatomic structure. As an input for this step, the first image data set, in this concrete example a reconstructed computer tomography data set of the thorax/abdomen area, is used. The first image data set is provided as an axial stack of sectional images. Using a landmark detection, which may be based on machine learning, the relevant axial image part, that is, a subset of the sectional images located between the uppermost position of the liver and the middle of the lower-positioned kidney, is determined.

In a second step, each of the extracted two-dimensional sectional images are used as input data for a trained function, in this case a deep neural network, whose output data is a sectional image of the same size, in this case a probability image. In the probability image, each pixel (data point) is assigned a predicted probability that this pixel is part of a finding.

Figure 4:
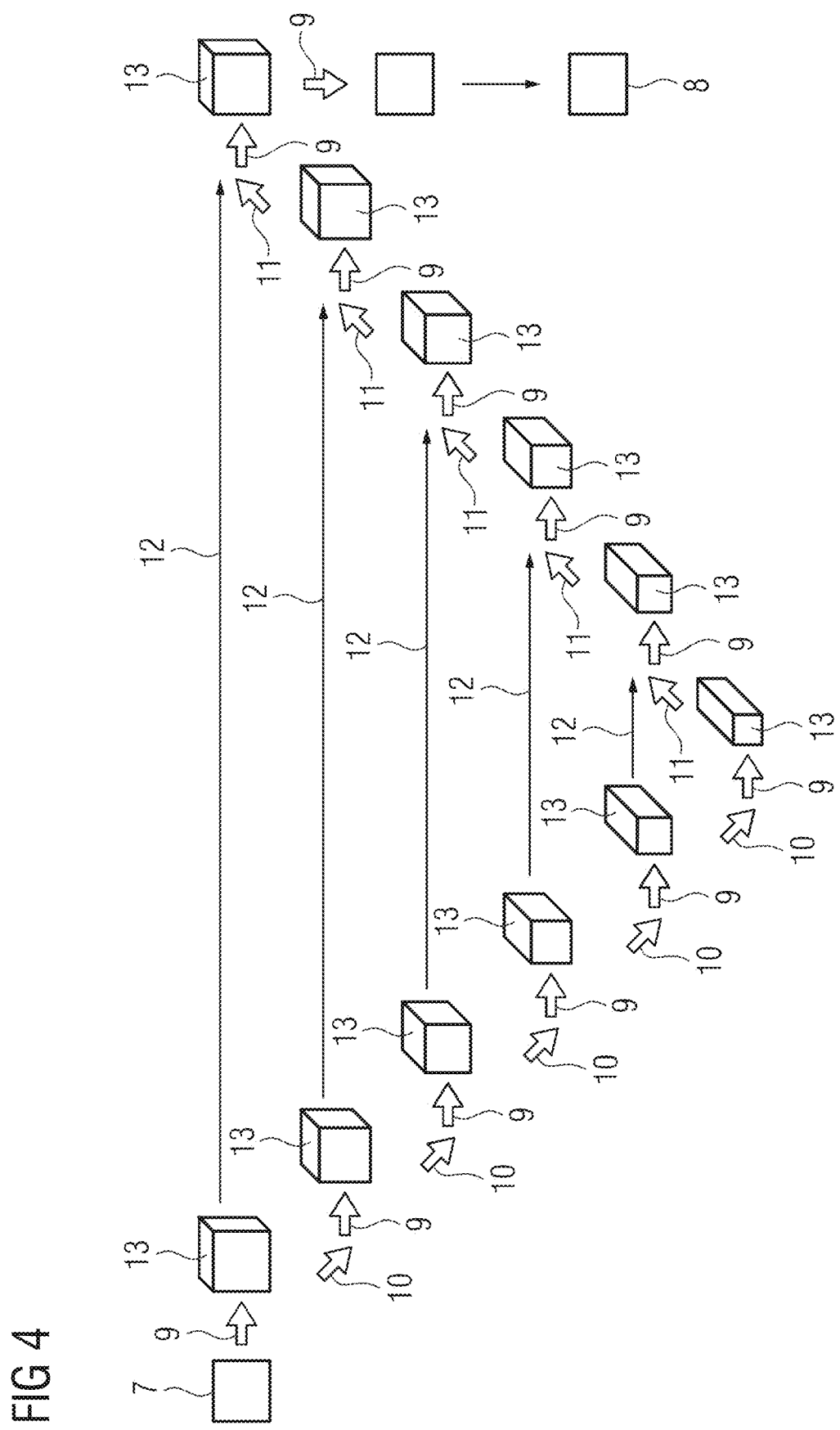

FIG. 4 shows an example topology of a deep neural network which can be used to determine probability images in this second step of the evaluation algorithm. The input data 7 are, as explained, axial sectional images of the first image data set, while the output data 8 are probability images. The arrows 9 each describe a layer performing the operation [convolution (3×3)+batch normalization+leaky ReLU]2, the arrows 10 symbolize a max-pooling layer (2×2), the arrows 11 indicate the operation of up-sampling (2×2)+convolution (3×3, depth/2) and the arrows 12 stand for skip connections. The respective boxes 13 indicate the evolution of the number of nodes, see as well the explanation with regard to FIG. 3.

Of course, also different topologies which are used for image segmentation problems may be employed. Regarding the training of the trained function, segmentation masks of adrenal gland findings, which have been generated by manual contouring, can be used.

In a third step of the evaluation algorithm, the probability images are interpreted to determine the presence of a finding and, if a finding is present, corresponding finding information. In this embodiment, the maximum of all probabilities in the probability images is compared to a first threshold. If the maximum probability exceeds this first threshold, the detection is determined as positive. Additionally, the location, where the maximum probability has been determined, is used as a location of the finding, and the sub-set of the pixels around this location whose predicted probabilities exceed a second threshold, is interpreted as defining the extensions of the finding, in particular its dimensions.

In an optional embodiment, if the first image data set has been acquired using dual-energy computer tomography, the characterisation of the finding can also be implemented. The spectral information in the area of the finding can be used as input data for a further trained function, in particular a further neural network, which determines, as output data, a malignancy probability for the finding, in particular the potential lesion. For such a neural network, any topology which is known for image classification problems may be used. The neural network can be trained on the basis of annotated benign and malign adrenal gland lesions and/or image artefacts.

Figure 5:
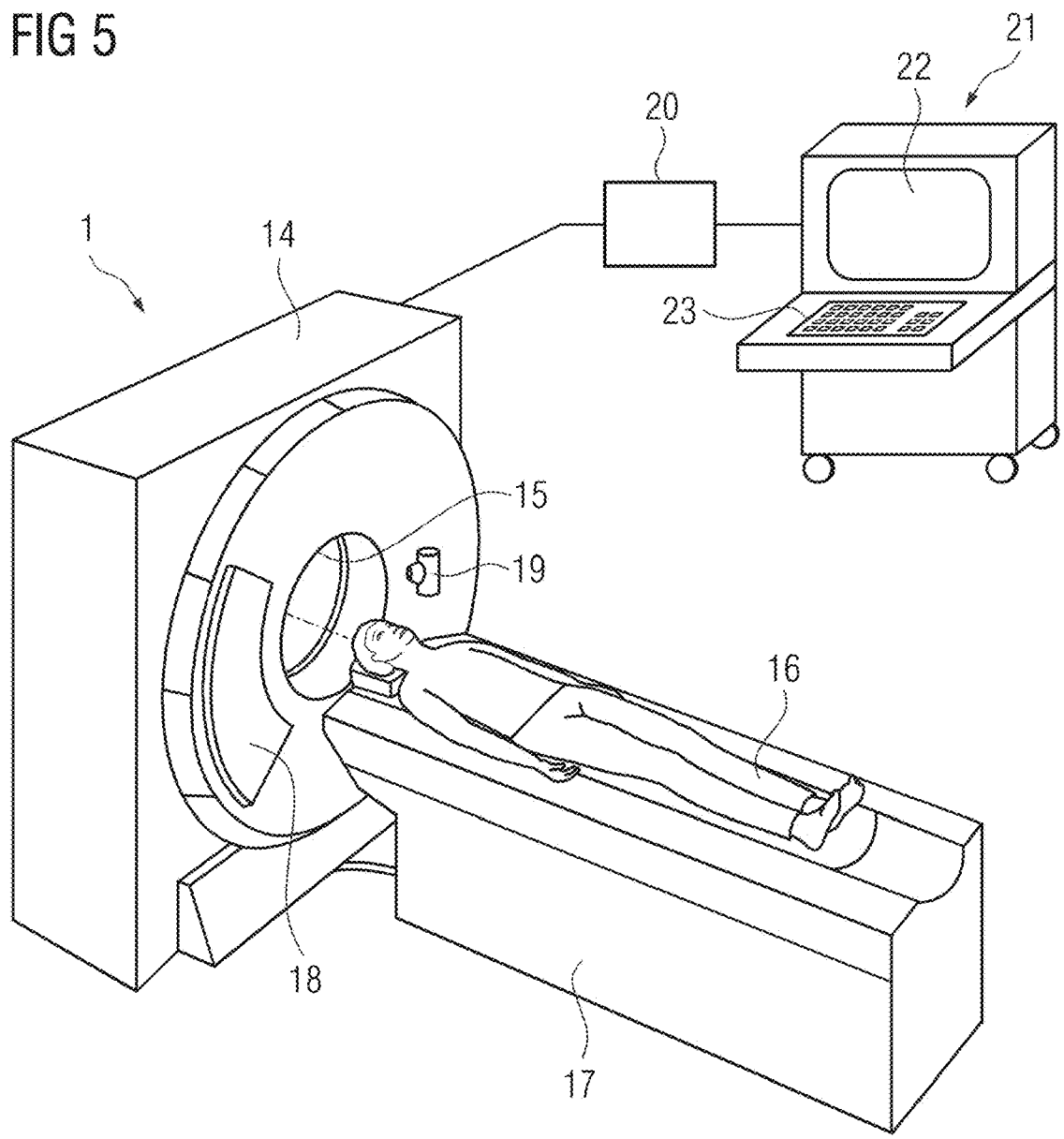

FIG. 5 shows an embodiment of a medical imaging apparatus 1 according to the present invention, in this case a computer tomography scanner. The medical imaging apparatus thus comprises a gantry 14 having an opening 15 for a patient 16 which may be positioned on a respective patient table 17. In the gantry 14, an x-ray detector 18 and an x-ray source 19 are rotatably mounted to scan the region of interest of the patient 16 positioned in the opening 15.

The operation of the medical imaging apparatus 1 is controlled by a control device 20, which is configured to perform a method according to the invention. The control device is also connected to a user interface 21 of the medical imaging apparatus 1, which in turn comprises an output device 22 and an input device 23. The user interface 21 may, for example, be a scanner work station.

The user interface 21 as well as other components of the medical imaging apparatus 1 may be connected to the control device via corresponding interfaces.

Figure 6:
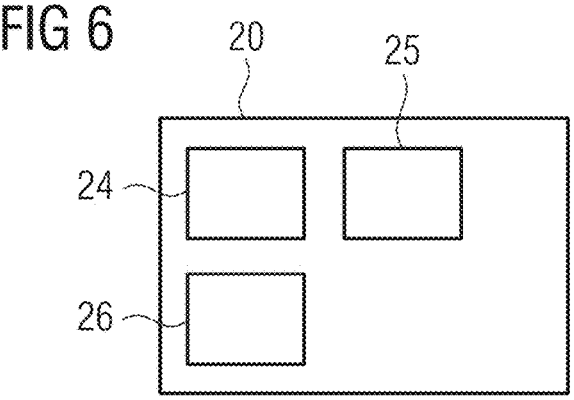

FIG. 6 shows the functional structure of the control device 20. In particular, the control device 20 comprises, as in principle known, an acquisition unit 24 controlling the acquisition of image data sets according to imaging parameters. The acquisition unit 24 may also include a reconstruction sub unit for reconstructing three-dimensional computer tomography data sets. The acquisition unit 24 is adapted to perform the step S1 in FIG. 1.

An evaluation unit 25 is provided to perform the step S2 according to FIG. 1. Triggered by the completion of the acquisition of a first image data set, the evaluation unit 25 applies the at least one evaluation algorithm to the first image data set to derive the evaluation information.

The input/output unit 26, among other tasks, is configured to notify the user 1 via the output device 22 if a finding is detected (steps S3 and S4 in FIG. 1) and to receive corresponding input from the input device 23, in particular a confirmation.

Although the present invention has been described in detail with reference to the preferred embodiment, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for operating a medical imaging apparatus, the medical imaging apparatus including a control device, an input device and an output device, during an examination process of a patient, the method comprising:
   acquiring a first image data set of a region of interest of the patient;
   automatically evaluating, by the control device, the first image data set using at least one evaluation algorithm yielding evaluation information regarding at least one type of finding, at least one of the at least one evaluation algorithm including a trained function trained by a machine learning algorithm, the evaluation information describing a presence or absence of at least one finding of a type in the first image data set, and the at least one finding requiring
   acquisition of a second image data set for further analysis, and
   at least one imaging parameter for the second image data set;
   automatically notifying a user, via the output device, of the required acquisition of the second image data set in response to the evaluation information indicating the presence of the at least one finding; and
   acquiring the second image data set in a same examination process, using the at least one imaging parameter of the evaluation information in response to confirmation of acquisition of the second image data set by the user.

2. The method of claim 1, wherein the at least one imaging parameter defines a complete acquisition protocol for the medical imaging apparatus, allowing completely automatic acquiring of the second image data set.

3. The method of claim 1, further comprising:
   at least one of modifying or defining at least one of the at least one imaging parameter or additional imaging parameters depending on a user input.

4. The method of claim 1, further comprising:
   training the trained function using annotated training data sets of the region of interest or subregions of the region of interest.

5. The method of claim 1, further comprising:
   extracting image data showing at least one anatomical structure from the first image data set for at least one of the at least one evaluation algorithm analyzing the at least one anatomical structure.

6. The method of claim 1, further comprising:
   determining by at least a part of at least one of the at least one evaluation algorithm, for each respective data point in analyzed image data of the first image data, a respective probability that the respective data point belongs to a finding of the at least one type.

7. The method of claim 6, further comprising:
   determining the presence of at least one finding in response to a maximum of the probabilities exceeding a first threshold value.

8. The method of claim 7, further comprising:
   determining a position of the data point of the maximum probability as at least one of a location of the at least one finding or an area surrounding the data point of the maximum probability in response to the presence of at least one finding being determined; and
   determining the position of the data point of the maximum probability as an extension of the at least one finding in response to the probability exceeding a second threshold.

9. The method of claim 1, further comprising:
   determining, by at least one of the at least one evaluation algorithm, finding information describing at least one finding whose presence has been determined; and
   at least one of choosing or adapting at least one of the at least one imaging parameter depending on the finding information.

10. The method of claim 9, further comprising:
    outputting at least a part of the finding information to the user.

11. The method of claim 1, further comprising:
    acquiring the first image data set and the second image data set using computed tomography.

12. A medical imaging apparatus, comprising:
an input device;
an output device; and
a control device including processing circuitry configured to cause the medical imaging apparatus to
  acquire a first image data set of a region of interest of a patient,
  automatically evaluate the first image data set using at least one evaluation algorithm yielding evaluation information regarding at least one type of finding, at least one of the at least one evaluation algorithm including a trained function trained by a machine learning algorithm, the evaluation information describing a presence or absence of at least one finding of a type in the first image data set, and the at least one finding requiring
  acquisition of a second image data set for further analysis, and
  at least one imaging parameter for the second image data set,
  automatically notify a user, via the output device, of the required acquisition of the second image data set in response to the evaluation information indicating the presence of the at least one finding, and
  acquire the second image data set in a same examination process, using the at least one imaging parameter of the evaluation information in response to confirmation of acquisition of the second image data set by the user.

13. A non-transitory electronically readable storage medium, storing computer program comprising instructions which, when the computer program is executed on a control device of a medical imaging apparatus, cause the control device to:
  acquire a first image data set of a region of interest of a patient;
  automatically evaluate the first image data set using at least one evaluation algorithm yielding evaluation information regarding at least one type of finding, at least one of the at least one evaluation algorithm including a trained function trained by a machine learning algorithm, the evaluation information describing a presence or absence of at least one finding of a type in the first image data set, and the at least one finding requiring
  acquisition of a second image data set for further analysis, and
  at least one imaging parameter for the second image data set;
  automatically notify a user, via an output device, of the required acquisition of the second image data set in response to the evaluation information indicating the presence of the at least one finding; and
  acquire the second image data set in a same examination process, using the at least one imaging parameter of the evaluation information in response to confirmation of acquisition of the second image data set by the user.

14. The method of claim 1, further comprising:
modifying a further examination process depending on at least one of the at least one imaging parameter to yield the second image data set, in response to a further acquisition already being planned during the examination process.

15. The method of claim 2, further comprising:
modifying a further examination depending on at least one of the at least one imaging parameter to yield the second image data set, in response to a further acquisition already being planned during the examination process.

16. The method of claim 2, further comprising:
at least one of modifying or defining at least one of the at least one imaging parameter or additional imaging parameters depending on a user input.

17. The method of claim 1, wherein the trained function comprises a deep neural network.

18. The method of claim 9, wherein the finding information describing the at least one finding whose presence has been determined, includes at least one of a location, extension, or characterization of the at least one finding.

* * * * *